United States Patent [19]

Merz et al.

[11] 4,205,384

[45] May 27, 1980

[54] METHOD FOR THE ANALYTIC DETERMINATION OF PHYSICAL CHARACTERISTICS OF A MATERIAL

[75] Inventors: Georg Merz, Gedern-Wenings; Heinz Gehrmann, Biebergemuend-Bieber, both of Fed. Rep. of Germany

[73] Assignee: WIBAU GmbH, Gruendau-Rothenbergen, Fed. Rep. of Germany

[21] Appl. No.: 937,959

[22] Filed: Aug. 30, 1978

[30] Foreign Application Priority Data

Sep. 14, 1977 [DE] Fed. Rep. of Germany ....... 2741321

[51] Int. Cl.² .......................................... G01N 33/16
[52] U.S. Cl. ................................ 364/555; 73/432 PS; 235/92 PC; 250/333
[58] Field of Search .................. 364/555, 514, 515; 235/92 PC; 324/71 CP; 250/333, 334, 342; 73/28, 30, 432 PS

[56] References Cited

U.S. PATENT DOCUMENTS

| | | | |
|---|---|---|---|
| 3,717,040 | 2/1973 | Guillet | 73/432 PS |
| 3,763,428 | 10/1973 | Preist | 235/92 PC |
| 3,860,804 | 1/1975 | Rutman | 364/555 |
| 3,932,839 | 1/1976 | Stephens | 235/92 PC |
| 3,936,666 | 2/1976 | Hogg et al. | 235/92 PC |
| 4,021,117 | 5/1977 | Göhde et al. | 235/92 PC |
| 4,031,393 | 6/1977 | Redman | 250/333 |
| 4,110,604 | 8/1978 | Haynes et al. | 235/92 PC |
| 4,128,884 | 12/1978 | England | 364/555 |

*Primary Examiner*—Errol A. Krass
*Attorney, Agent, or Firm*—W. G. Fasse; D. F. Gould

[57] ABSTRACT

The present method provides a determination of physical characteristics of materials. For example, the granulometry of a falling or flowing stream of disperse material may be analytically determined by a heat image camera cooperating with a memory such as a screen type image storage, a monitor, and a process computer such as a microcomputer which compares the measured values with a reference value to provide a control signal. A control apparatus regulates the flow rate of the material stream, such as aggregate, in response to said control signal. The present method may be used to determine, for example, the size of falling liquid droplets or the size of the particles of granular material which is stationary in a measuring zone or space.

11 Claims, 1 Drawing Figure

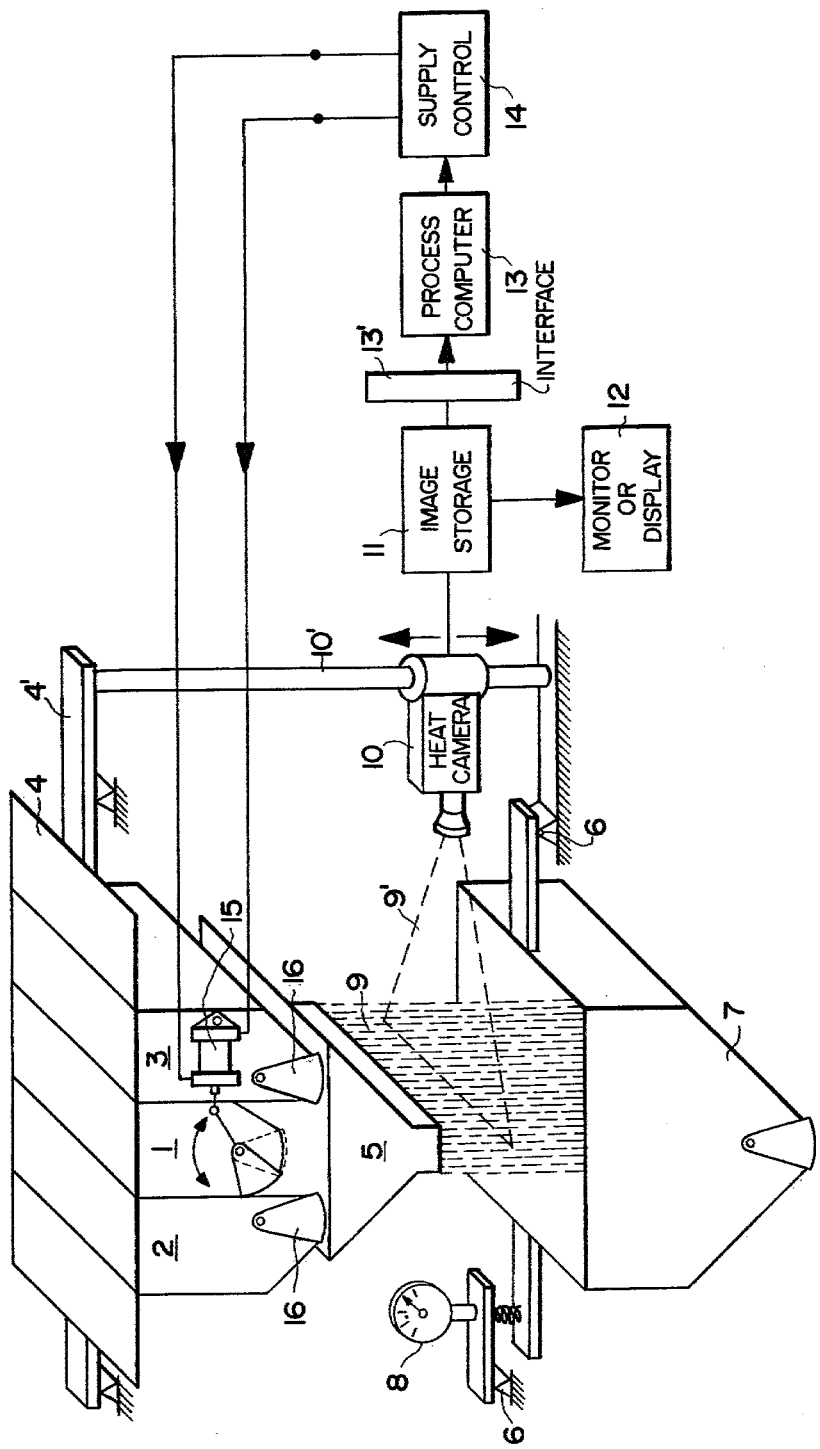

METHOD FOR THE ANALYTIC DETERMINATION OF PHYSICAL CHARACTERISTICS OF A MATERIAL

BACKGROUND OF THE INVENTION

The invention relates to a method for the analytic determination of physical characteristics of a material. More specifically, the invention relates to determining the "granulometry" of a flowing or falling stream of material such as granular material or a dispersed liquid moving in the form of droplets. This method is especially suitable for determining the grain size of dry solid materials such as aggregate or for determining the size of falling drops of liquid. The material in the case of solid materials may be stationary in a measuring zone or the material such as granular material or liquid droplet may move between a delivery station and a receiving station. The physical characteristics, once they have been determined may be used for further evaluation or display and for control purposes, for example, in connection with the control of the material supply through the measuring zone.

The term "granulometry" in this context is supposed to mean the ascertaining of the various size ranges of particles making up a granular material such as aggregate.

The German Patent (DT-PS) No. 1,140,355 describes a weight monitoring apparatus for maintaining the mixing ratio of a dry component in a mixture. In said prior art method a predetermined partial quantity of material is intermittently removed from a flowing stream of material and sorted according to size. The result of such sorting is used to control, in a closed loop fashion, the output or discharge of the material from the individual supply bins.

In this known apparatus, a collection container is arranged downstream of each sorting device for each material component. The outflow of all collection containers is supplied into a common weighing apparatus. The content of the collection containers is weighed one after the other, and the result of the weighing is used as a control value for controlling the outflow of the supply bins.

Such prior art method has a number of substantial disadvantages. For example, the time for the sorting, weighing and evaluating for the purpose of correcting the supply of material is relatively long. Hence, the output of the supply bins in response to the sorting result may occur only after several minutes have passed, at which time a stream of material is being controlled, which already deviates considerably from the sorting result based on the prior sample taking.

The use of said prior art apparatus in connection with a preparation plant for the manufacture of a bituminous mixture is especially critical. Since only dried mineral materials may be used for making a reasonably exact screen analysis, the sample may be taken only after passage of the mineral materials through a rotary drum dryer, the resulting correction time is often in the order of about ten minutes. In other words, a condition is being changed or influenced which had already appeared ten minutes earlier, and generally is no longer present. Hence, the known apparatus is not useful for the purpose of screen analysis.

Furthermore, the true control of components ranging in size from 0 to 2 mm is not possible. Take, for example, the mean values of the constituents ranging from 0 to 2 mm for a so-called asphalt fine concrete which is rich in crushed stone according to governmental regulations in the Federal Republic of Germany. Accordingly, after the removal of the filler material the mean grading curve of the sand component is made up as follows.

TABLE I

| sand component size in 0-2 asphalt fine concrete Constitutent size (mm) | | |
|---|---|---|
| min | max | % |
| 0.09 | 0.25 | 12 |
| 0.25 | 0.71 | 13.5 |
| 0.71 | 2.00 | 13.5 |
| Total sand in the mixture | | 39% |

In the case of asphalt fine concrete which is poor in crushed rock and which has a sand component in the range of 0 to 8 mm, the following picture may be obtained for the sand component again after removal of the filler: results:

TABLE II

| sand component size in 0 to 8 mm asphalt fine concrete component range in mm | | |
|---|---|---|
| min | max | % |
| 0.09 | 0.25 | 25.5 |
| 0.25 | 0.71 | 18.5 |
| 0.71 | 2.00 | 17.0 |
| Total sand in the mixture | | 61% |

The foregoing tables mean that the composition of 40 to 60% of the mixture portion is not controllable by means of a quick screen analysis. In the case of mixtures rich in crushed stone, the problem is somewhat simpler since in such mixtures the sand is made up of three approximately equal portions. The problem is more critical in the case of asphalt mixtures poor in crushed stone, since the fine sands in the size range from 0.09 to 0.25 mm are present in a considerably larger proportion in comparision to the two other components of the total sand proportion.

If one considers all of the factors influencing the degree of quality of the screen analysis, such as the method of operation of the screening machine, the type of granularity, the mesh size, the screening duration, and particularly the quantity of screened material or the screen throughput, the monitoring of a stream of granular solid materials to be sorted with respect to its required granulometry becomes even more problematic particularly in the case of fluctuating throughputs. Although the above examples relate to bituminous mixtures the respective conclusions are relevant to the preparation or the bringing together of all building material mixtures. Beyond that, these conclusions are relevant to the combination of all solids in various classes of granulation or grain sizes.

OBJECTS OF THE INVENTION

In view of the above it is the aim of the invention to achieve the following objects singly or in combination:

to provide a method for analytically determining the physical characteristics of a material, for example, granulometry or grain size composition of a flowing or falling disperse stream of material whereby time delays are to be substantially avoided;

to provide a method for determining the size of liquid droplets, especially falling liquid droplets, substantially without time delay;

- to avoid the time delay caused by the intermittent taking of a sample and the screen sizing thereof;
- to avoid the unsatisfactory evaluation or rather utilization of the screening result by belatedly influencing the stream of material at the supply end thereof;
- to provide for a true comparison of measured values with a rated value, such as a screen size value;
- to provide for a practically instantaneous determination of the result or results and the respective utilization of such results for control purposes; and
- to provide a method wherein effects related to the material which is being analyzed, to structural factors, and to capacity considerations, which could be especially operative on the selectivity or resolution, do not influence the result of the analysis.

SUMMARY OF THE INVENTION

The above objects have been achieved according to the present invention in a method which determines or ascertains physical characteristics of materials, such as granular materials or liquids dispersed in droplet form. The granular material or droplets may be falling or flowing through a measuring zone, the granular material may even be in a stationary distribution in said measuring zone which constitutes a measuring field or a measuring space wherein the material is exposed to a sensor device, such as a heat image camera which instantaneously detects during the stay of the materials within said measuring field or measuring space, said characteristics in the form of measured values representing, for example, the size and/or the mass and/or the heat content or possibly other features of the granules or droplets. One or several sensors may be used. Several sensors may be effective in the same or in different directions. The measured values are sorted into individual predetermined ranges, whereupon the values within each range as summed or added. The summed values are stored. The values are then individually, or in addition or in combination with other measured values of the respective range, stored in a retrievable manner for displaying and/or evaluating.

In a preferred embodiment of the invention the passage of the particles or droplets through the measuring field or through the measuring space is recorded by said heat image camera operating as a detection or sensor means in a continuous repetition during the duration of the analysis. The information is then transmitted to a screen type image storing device and evaluated by counting the respective image lines which are coherent and thus form groups. The result is then sorted and recallably or retrievably stored.

With the aid of this method, the granulometry of disperse solid bodies, that is, of particles within a plane or space may be instantly and within a short time repeatably determined, displayed and evaluated, whereby the determination, displaying and evaluation may be repeated many times. In this connection and as stated above, the material need not flow or fall; a stationary distribution may also be evaluated, however, the repetition thereof would bring no additional information.

The sorting then follows, as usual, according to the determined dimensions. It is to be understood, however, that other criteria may also be used for the sorting. Hence, the specific heat and the temperature of the particles during an image sensing may be taken as a constant value for given homogeneous or uniform material, so that the intensity of the radiation resulting from the heat content of the particles may also be of assistance for the sorting. However, this is only an example illustrating the possibilities.

The possible taking and evaluation sequence of about ten temperature images per second is so short in time, that it is not necessary in some instances to exhaust the full capacity of the present method. Thee are not mechanically or operationally related limitations with respect to the quality of the analysis in the use of this method. As mentioned, the method is also completely suitable for determining the size of moving, for instance, falling drops of liquid.

BRIEF FIGURE DESCRIPTION

In order that the invention may be clearly understood, it will now be described by way of example, with reference to the accompanying drawings, wherein the single FIGURE shows a schematic diagram of the present method steps whereby the apparatus features are shown in block form since the apparatus components are known as such.

DETAILED DESCRIPTION OF PREFERRED EXAMPLE EMBODIMENTS

The invention will be explained by means of a schematic illustration showing several supply bins 1, 2, and 3 forming a bin group 4 supported by a frame 4' and cooperating with a funnel 5 arranged below the bottoms of the bins 1, 2, 3.

The bin bottoms may be opened and closed to any desired extent by members 16 under the control of piston cylinder and lever means 15 only one of which is shown for simplicity. The funnels associated with said supply bins 1, 2, 3, lead into a weighing box 7. However, a measuring zone 9 is formed beneath the funnel output between the funnel and the weighing box. The measuring zone 9 or rather a field 9' is monitored by a temperature image camera 10 which may be slidable up and down for adjustment along a pole 10' of the frame 4'.

As mentioned, the feed bins 1, 2, and 3 are combined into a bin group 4 supported by the frame 4 merely schematically shown. The same pertains to the funnel 5 and to the pivots 6 of the scales 8 connected to the weighing box 7. The components 4 to 6 all have a fixed relationship to each other.

The measuring field 9' or the measuring space 9 is defined between the output of the funnel 5 and the entrance to the weighing box 7. The temperature image camera 10 is securely but adjustably attached to the pole 10'. A set screw may hold the camera housing in any desired position along the pole 10'.

In operation, the temperature image camera 10 scans the measuring field or plane 9' or several such cameras scan the measuring space 9. Each camera 10 converts the heat signals to electrical signals which are pictorially represented as light signals on a display monitor 12. Simultaneously, the electrical signals stored in the screen type image storage 11 may be picked up by a process computer 13 connected in parallel through an interface 13' to the storing image screen or screens 11 when the method is used for controlling material processes. The process computer 13 such as a microcomputer has, for example, the function to compare the determined result with a rated or reference value set in or supplied to a comparator forming part of the microprocessor whereby the difference value may be used as the control value for the activation of the control unit 14 such as solenoid operated valves for actuating piston cylinder drive means 15 for the closure members 16. Thus, a practically instantaneous change in the amount of granular material supplied through the measuring field 9' or the measuring space 9 is achieved, to match the measure value with the rated or reference value to make the difference approach zero.

Since the images are representations of respective areas and since the spatial component is to be considered as an empirical factor, it is useful if the measured values which characterize the surface sizes of the particles and which are determined in one plane of the measuring field 9' or space 9, are combined with given values which characterize the depth measures and which take into account the ascertained distribution curve to form a spatial measured value. The first mentioned measured values are then sorted according to this spatial value.

The scope of the possible imponderables may thereby be considered to be extremely small and these imponderables may be considerably reduced still further, if the passage of the particles through the measuring space 9 during the analysis is detected by several synchronously triggered heat image cameras 10 arranged in different planes 9'. These passges or rather images are transmitted to screen type image storing means 11 associated with each camera 10.

The image lines in each plane are counted and the results of such image line counting are compensated by computation, with the corresponding images of the same particles from the other planes. The result of the compensation is sorted and stored in a retrievable manner. The stored contents may be displayed independently of the storing by means of a corresponding display monitor 12.

This present invention allows a nearly unambiguous sorting according to volume. An embodiment of this type, however, will not be necessary in a majority of the possible uses of the present method.

Incidentally, the components used for performing the present method are known as such as may be seen from the following list:

| Reference number | Item | Model Number | Manufacturer |
| --- | --- | --- | --- |
| 10 | heat image camera | TH 7506 | Thomson, CSF Rennbahnstr.6 6 Frankfurt-71 |
| 11 | screen type image storage | VM-7801 | MERZ-electronic 6463 Gedern |
| 12 | monitor and/or display | MO-152 135 | WIBAU Hartmann AG 6466 Grundau-Rothenbergen |
| 13' | interface | MPS-01.1 | WIBAU Hartmann AG 6466 Grundau-Rothenbergen |
| 13 | process computer | MPS-01 | WIBAU Hartmann AG 6466 Grundau-Rothenbergen |
| 14 | supply control | LK-152 101 | WIBAU Hartmann AG 6466 Grundau-Rothenbergen |

Although the invention has been described with reference to specific example embodiments, it is to be understood that it is intended to cover all modifications and equivalents within the scope of the appended claims.

What is claimed is:

1. A method for the analytic determination of physical characteristics of a material, comprising the following steps: establishing a measuring zone, moving said material through said measuring zone, training sensor means in the form of heat image camera means for measuring said physical characteristics, onto said measuring zone, repeatedly operating said heat image camera means when said material is moving through said measuring zone to provide measured values representing said physical characteristics, said operating of said heat image camera means taking place during a predetermined time period to provide a number of heat image lines representing said physical characteristics, transferring the heat image lines onto a screen type image storage means, sorting said heat image lines into predetermined value ranges, summing the heat image lines within each value range to form individual sum values for the respective ranges by counting the heat image lines in groups whereby the groups are formed by coherent image lines for evaluation, and sorting the individual range sum values in a retrievable manner for display or evaluation.

2. The method of claim 1, wherein said physical characteristics represent the grain size of granular material.

3. The method of claim 1, wherein said physical characteristics represent the mass of said material.

4. The method of claim 1, wherein said physical characteristics represent the heat content of said material.

5. The method of claim 1, wherein said physical characteristics represent the droplet size of a liquid.

6. The method of claim 1, wherein said measured values represent surface area values of material particles or droplets in a plane of said measuring zone, said method further comprising providing predetermined factor values, multiplying said surface area representing values with said predetermined factor values, and then performing said sorting and storing.

7. The method of claim 6, wherein said predetermined factor values represent a distribution frequency of said surface area valves and a length value of said particle or droplet sizes whereby said multiplying of said surface area values with said length value provides a volume characteristic of said material.

8. The method of claim 1, wherein said moving of said material through said measuring zone takes place at a controllable supply rate, said method further comprising providing process computer means and connecting said process computer means to said screen type image storage means through suitable interface means, providing a reference value for said supply rate, comparing said stored measured values with said reference value in said process computer means to provide a difference value, and using the difference value for varying said supply rate in such a direction that said difference value approaches zero, whereby the measured value is adapted to the reference value.

9. The method of claim 8, further comprising operatively connecting monitor means to each screen type image storage means and retrieving the stored values from said storage means in repeated cycles through the respective monitor means.

10. A method for the analytic determination of physical characteristics of a material, comprising the following steps: establishing a measuring zone as a defined space, passing said material in the form of granules or droplets through said space, training sensor means, comprising a plurality of heat image cameras, on different planes in said defined space, repeatedly operating said heat image cameras in synchronism, transferring the heat images of each heat image camera onto a respective screen type image storage means, counting the image lines of each image in each plane to provide respective values for said different planes, mathematically combining said values relating to said granules or droplets as they move through said different planes, the combined values and then storing the sorted and combined values in a retrievable manner.

11. The method of claim 10, wherein said granules or droplets are passed through said measuring zone by the force of gravity.

* * * * *

UNITED STATES PATENT OFFICE
CERTIFICATE OF CORRECTION

Patent No. 4,205,384  Dated May 27, 1979

Inventor(s) Georg Merz et al

It is certified that error appears in the above-identified patent and that said Letters Patent are hereby corrected as shown below:

In claim 1 (column 6, line 23) "sorting" should be --storing--.

In claim 7, (column 6, line 43) "valves" should be --values--.

In claim 10, (column 8, line 2) after "planes," --sorting-- should be inserted.

Signed and Sealed this

Fifth Day of August 1980

[SEAL]

Attest:

SIDNEY A. DIAMOND

Attesting Officer  Commissioner of Patents and Trademarks